(12) United States Patent
Tsukada et al.

(10) Patent No.: US 9,872,928 B2
(45) Date of Patent: Jan. 23, 2018

(54) DIAGNOSTIC AGENT FOR THERAPEUTIC EFFECT ON CANCER

(71) Applicant: HAMAMATSU PHOTONICS K.K., Hamamatsu-shi, Shizuoka (JP)

(72) Inventors: Hideo Tsukada, Hamamatsu (JP); Masakatsu Kanazawa, Hamamatsu (JP); Norihiro Harada, Hamamatsu (JP); Shingo Nishiyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/029,012

(22) PCT Filed: Sep. 18, 2014

(86) PCT No.: PCT/JP2014/074738
§ 371 (c)(1),
(2) Date: Apr. 13, 2016

(87) PCT Pub. No.: WO2015/056521
PCT Pub. Date: Apr. 23, 2015

(65) Prior Publication Data
US 2016/0256578 A1    Sep. 8, 2016

(30) Foreign Application Priority Data

Oct. 16, 2013   (JP) ................. 2013-215636

(51) Int. Cl.
*A61K 51/04*        (2006.01)
(52) U.S. Cl.
CPC ................. *A61K 51/0459* (2013.01)
(58) Field of Classification Search
CPC .................. A61K 31/50; A61K 51/00
See application file for complete search history.

(56) References Cited

FOREIGN PATENT DOCUMENTS

| CN | 102336741 A | | 2/2012 |
|---|---|---|---|
| EP | 0199281 A2 | | 10/1986 |
| EP | 665223 | * | 1/1995 |
| JP | 2009-504849 A | | 2/2009 |
| JP | 2013-518913 A | | 5/2013 |
| WO | WO-2014/026079 A2 | | 2/2014 |
| WO | WO-2014/030709 A1 | | 2/2014 |

OTHER PUBLICATIONS

Norihiro Harada et al., Development of novel PET probes, [18F]BCPP-EF, [18F]BCPP-BF, and [11C]BCPP-EM for mitochondrial complex 1 imaging in the living brain, J. of label Compd. Radiopharm, 2013, 56, 553-561.*

Roko Kubota et al., "Intratumoral Distribution of Fluorine-18-Fluorodeoxyglucose In Vivo: High Accumulation in Macrophages and Granulation Tissues Studied by Microautoradiography," The Journal of Nuclear Medicine, Nov. 1992, pp. 1972-1980, vol. 33, No. 11.

Masahiro Sugiyama et al., "Evaluation of 3'-Deoxy-3'-$^{18}$F-Fluorothymidine for Monitoring Tumor Response to Radiotherapy and Photodynamic Therapy in Mice," The Journal of Nuclear Medicine, Oct. 2004, pp. 1754-1758, vol. 45, No. 10.

Chieko Murayama et al., "Evaluation of $_D$-$^{18}$F-FMT, $^{18}$F-FDG, $_L$-$^{11}$C-MET, and $^{18}$F-FLT for Monitoring the Response of Tumors to Radiotherapy in Mice," The Journal of Nuclear Medicine, Feb. 2009, pp. 290-295, vol. 50, No. 2.

Norihiro Harada et al., "Development of novel PET probes, [$^{18}$F]BCPP-EF, [$^{18}$F]BCPP-BF, and [$^{11}$C]BCPP-EM for mitochondrial complex 1 imaging in the living brain," Journal of Labelled Compounds and Radiopharmaceuticals, 2013, pp. 553-561, vol. 56, published on-line in Wiley Online Library, http://onlinelibrary.wiley.com/doi/10.1002/jlcr.3056.

Norihiro Harada et al., "P-337 Development of novel PET probes, [$^{18}$F]BCPP-EF, [18F]BCPP-BF, and [$^{11}$C]BCPP-EM for mitochondrial complex 1 imaging," S-424 20th International Symposium on Radiopharmaceutical Sciences, Journal of Labelled Compounds and Radiopharmaceuticals, Jul. 30, 2013, p. 337, vol. 56, published on-line in Wiley Online Library, http://onlinelibrary.wiley.com/doi/10.1002/jlcr.3054.

International Preliminary Report on Patentability dated Apr. 19, 2016 for PCT/JP2014/074738.

Juweid et al., "Use of Positron Emission Tomography for Response Assessment of Lymphoma: Consensus of the Imaging Subcommittee of International Harmonization Project in Lymphoma", Journal of Clinical Oncology, vol. 25, No. 5, 2007, p. 571-p. 578.

(Continued)

*Primary Examiner* — Michael G Hartley
*Assistant Examiner* — Jagadishwar Samala
(74) *Attorney, Agent, or Firm* — Drinker Biddle & Reath LLP

(57) ABSTRACT

The present invention provides a diagnostic agent for a therapeutic effect on cancer, containing a compound represented by formula (1-0).

(1-0)

(In formula (1-0), R represents —O(CH$_2$)$_n$—, —O(CH$_2$)$_n$OC$_2$H$_4$—, —CH$_2$O(CH$_2$)$_n$—, or —CH$_2$O(CH$_2$)$_n$OC$_2$H$_4$—, n represents an integer of 1 to 5, and Q$^1$ represents F or —OCH$_3$.)

12 Claims, 4 Drawing Sheets

(56) References Cited

OTHER PUBLICATIONS

Pauwels, E. K. J., et al., "Fluorine-18-radiolabeled pharmaceuticals for imaging with positron emission tomography, excluding [$^{18}$F]-fluorodeoxyglucose", Drugs of the Future, Prous Science, ES, vol. 27, No. 7, Jan. 1, 2002, p. 655-p. 667, XP002432635.

DePaepe, Boel, "Mitochondrial Markers for Cancer: Relevance to Diagnosis, Therapy, and Prognosis and General Understanding of Malignant Disease Mechanisms", ISRN Pathology, vol. 2012, Jan. 1, 2012, p. 1-p. 15, XP055366885.

Chieko Murayama, et al., "Monitoring Mitochondrial Complex-I Activity Using Novel PET Probe $^{18}$F-BCPP-EF Allows Early Detection of Radiotherapy Effect in Murine Squamous Cell Carcinoma", PLOS ONE, vol. 12, No. 1, Jan. 26, 2017, pp. 1-14, XP055366890.

\* cited by examiner

DIAGNOSTIC AGENT FOR THERAPEUTIC EFFECT ON CANCER

TECHNICAL FIELD

The present invention relates to a diagnostic agent for a therapeutic effect on cancer.

BACKGROUND ART

Positron emission tomography (PET method) has better sensitivity, resolution, and quantitativeness than single-photon tomography (SPECT method), and therefore is attracting attention particularly in recent years.

For example, a neuropsychiatric disease is currently diagnosed by evaluating glucose metabolism of nerve cells by the PET method. In this instance, as a PET probe, $^{18}$F fluorodeoxyglucose ([$^{18}$F]FDG) is used.

Furthermore, diagnosis (judgement) of a therapeutic effect on cancer by the PET method is also attempted (Non-Patent Literatures 1 to 3).

CITATION LIST

Non Patent Literatures

Non Patent Literature 1: Kubota R. et al., J Nucl Med 33 (1992) 1972-1980.
Non Patent Literature 2: Sugiyama M. et al., J Nucl Med 45 (2004) 1754-1758.
Non Patent Literature 3: Murayama C. et al., J Nucl Med 50 (2009) 290-295.

SUMMARY OF INVENTION

Problems to be Solved by the Invention

However, [$^{18}$F]FDG is incorporated not only into a cancer cell but also into an activated immune cell (macrophage, microglia, or the like) induced by a therapy on cancer (cancer therapy). Therefore, it has been reported that the PET method using [$^{18}$F]FDG as a probe is not suitable for diagnosis of a therapeutic effect on cancer particularly at an early stage after starting of a cancer therapy (two to ten days after starting of the therapy) (Non-Patent Literatures 1 to 3).

On the other hand, it is very important to early diagnose a therapeutic effect of whether a selected cancer therapy is suitable for a patient as a subject in order to select a more effective therapy having less side effects and to improve a quality of life (QOL) of the patient as a subject.

The present invention has been accomplished in view of the above circumstances, and an object thereof is to provide a diagnostic agent for a therapeutic effect on cancer, being able to diagnose a therapeutic effect at an early stage after starting of a cancer therapy.

Means for Solving the Problems

The present inventors made intensive studies. As a result, the present inventors have found that a cancer cell undergoing apoptosis can be detected specifically by using a specific compound as a probe, and have completed the present invention.

That is, the present invention provides a diagnostic agent for a therapeutic effect on cancer, containing a compound represented by formula (1-0).

[Chemical formula 1]

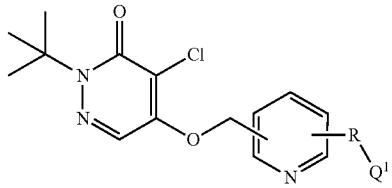

(1-0)

(In formula (1-0), R represents —O(CH$_2$)$_n$—, —O(CH$_2$)$_n$OC$_2$H$_4$—, —CH$_2$O(CH$_2$)$_n$—, or —CH$_2$O(CH$_2$)$_n$OC$_2$H$_4$—, n represents an integer of 1 to 5, and Q$^1$ represents F or —OCH$_3$.)

The diagnostic agent can detect a cancer cell undergoing apoptosis specifically, and therefore can diagnose a therapeutic effect at an early stage after starting of a cancer therapy.

The compound may be represented by formula (1-0').

[Chemical formula 2]

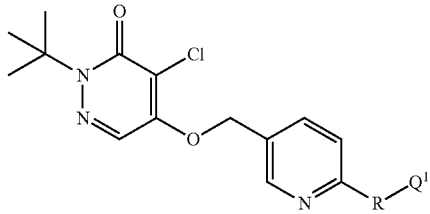

(1-0')

In the compound, Q$^1$ may be 18F or —O$^{11}$CH$_3$. The compound can thereby emit a positron. A positron emitted from the compound is bonded to an electron immediately and emits a γ ray (annihilation radiation). By measuring this γ ray with an apparatus used for the PET method, biodistribution of the compound can be imaged quantitatively with time. That is, a therapeutic effect on cancer can be diagnosed by the PET method.

The diagnostic agent containing a compound (1-0) in which Q$^1$ is $^{18}$F or —O$^{11}$CH$_3$ can be used suitably for the positron emission tomography.

Another aspect of the present invention provides a method for diagnosing a therapeutic effect on cancer, including a step of performing a cancer therapy to a subject contracting cancer, a step of administering a compound represented by formula (1-0) to the subject, a step of detecting the compound in the cancer, and a step of analyzing an accumulation amount of the compound in the cancer quantitatively.

Still another aspect of the present invention provides a compound represented by formula (1-0) for diagnosing a therapeutic effect on cancer.

Still another aspect of the present invention provides a compound represented by formula (1-0) for use as a diagnostic agent for a therapeutic effect on cancer.

Still another aspect of the present invention provides application of a compound represented by formula (1-0) for use in diagnosing a therapeutic effect on cancer.

Still another aspect of the present invention provides use of a compound represented by formula (1-0) in manufacturing a diagnostic agent for a therapeutic effect on cancer.

Effects of the Invention

The present invention makes it possible to provide a diagnostic agent for a therapeutic effect on cancer, being able to diagnose a therapeutic effect at an early stage after starting of a cancer therapy.

EMBODIMENTS FOR CARRYING OUT THE INVENTION

Figure 1:
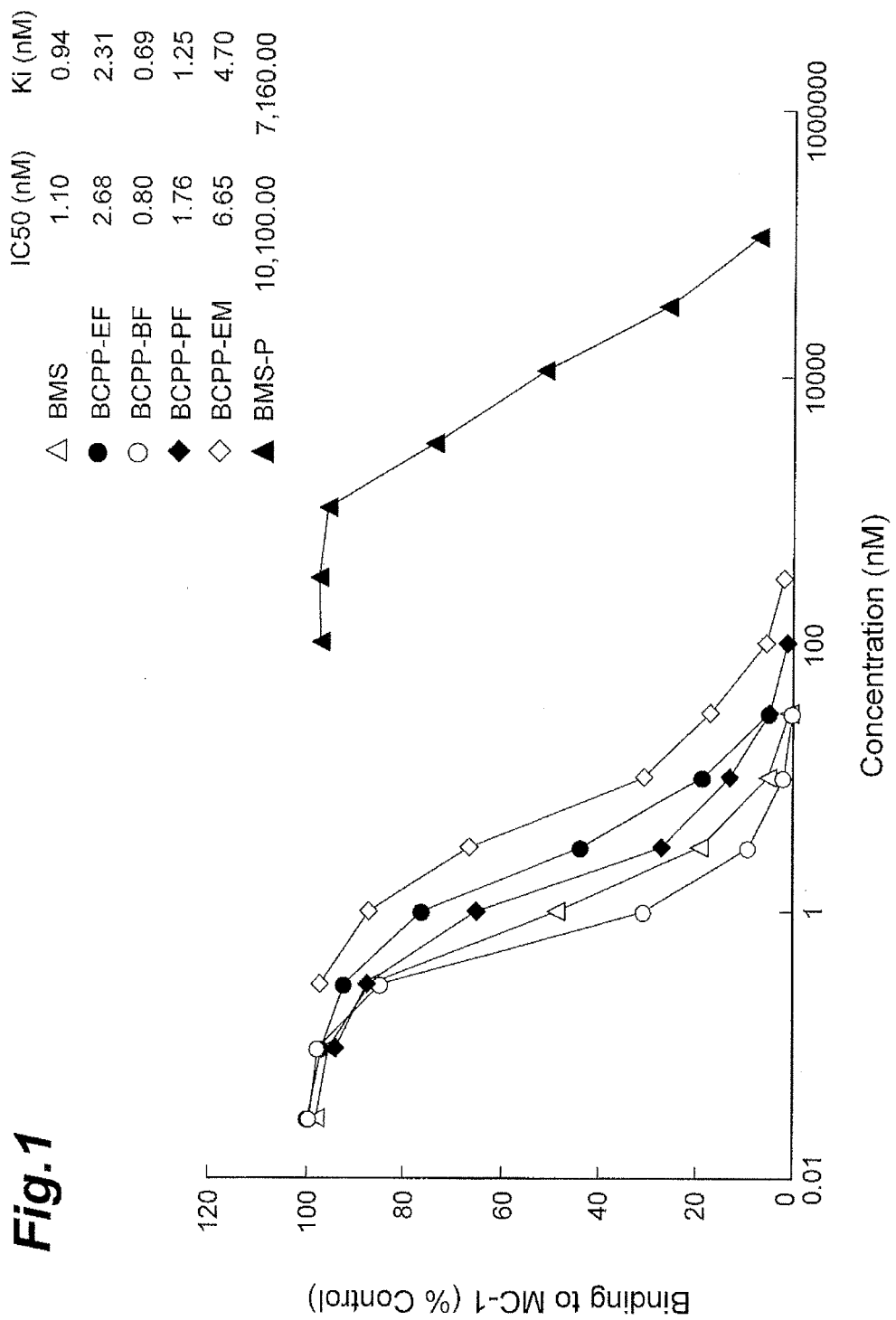
FIG. 1 is a graph illustrating a binding affinity with respect to mitochondria Complex-1.

Hereinafter, a preferred embodiment of the present invention will be described in detail. However, the present invention is not limited to the following embodiment.

A diagnostic agent for a therapeutic effect on cancer (hereinafter, also referred to simply as "diagnostic agent") according to the present embodiment contains a compound represented by formula (1-0) (hereinafter, also referred to as "compound (1-0)").

[Chemical formula 3]

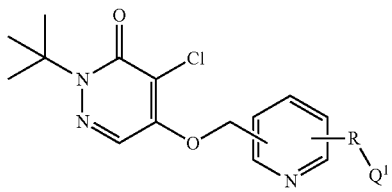

(1-0)

Here, the "diagnostic agent for a therapeutic effect on cancer" means a medical agent for diagnosing the degree of an effect of a therapy on a cancer cell or a tumor tissue. The "diagnostic agent for a therapeutic effect on cancer" means a medical agent which can detect a cancer cell in which an electron transport system involving MC-1 is activated and apoptosis is induced. In other words, the "diagnostic agent for a therapeutic effect on cancer" can be also understood as an agent for detecting apoptosis in a cancer cell.

Next, the compound (1-0) will be described. R represents —O(CH$_2$)$_n$—, —O(CH$_2$)$_n$OC$_2$H$_4$—, —CH$_2$O(CH$_2$)$_n$—, or —CH$_2$O(CH$_2$)$_n$OC$_2$H$_4$—. n represents an integer of 1 to 5, and may be 2 to 4. Q$^1$ represents F or —OCH$_3$, and may be $^{18}$F or —O$^{11}$CH$_3$. When Q$^1$ is —O$^{11}$CH$_3$ or $^{18}$F, the compound (1-0) can emit a positron. When Q$^1$ is —O$^{11}$CH$_3$, measurement can be performed a plurality of times in one day because the half-life is as short as 20 minutes. When Q$^1$ is $^{18}$F, measurement time at one time can be longer because the half-life is 110 minutes, which is longer than that of —O$^{11}$CH$_3$. At the same time, a compound (1-0) in which Q$^1$ is $^{18}$F can be supplied (delivered) from a manufacturing site having a cyclotron to a plurality of other measurement sites.

In a pyridine ring, a bonding position of —OCH$_2$— bonded to a pyridazine ring or a bonding position of R is not particularly limited, but the bonding position of —OCH$_2$— bonded to the pyridazine ring may be a 5-position, and the bonding position of R may be a 2-position. When the bonding position of —OCH$_2$— bonded to the pyridazine ring is a 5-position and the bonding position of R is a 2-position, a structural formula is indicated below as formula (1-0′).

[Chemical formula 4]

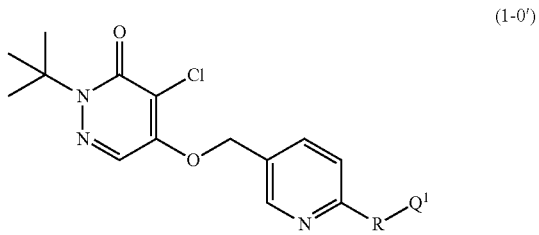

(1-0′)

The compound (1-0) may be a compound represented by formula (1) (hereinafter, also referred to as "compound (1)") from a viewpoint of bonding specificity with respect to mitochondria Complex-1.

[Chemical formula 5]

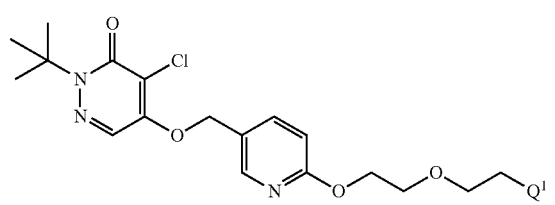

(1)

The compound (1-0) may be a compound represented by formula (1-2) (hereinafter, also referred to as "compound (1-2)") from a viewpoint of bonding specificity with respect to mitochondria Complex-1.

[Chemical formula 6]

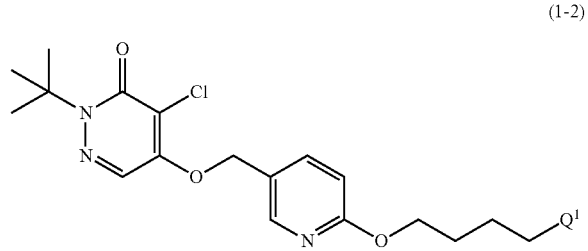

(1-2)

A compound represented by formula (2-0) (hereinafter, also referred to as "compound (2-0)") is a precursor of the compound (1-0).

[Chemical formula 7]

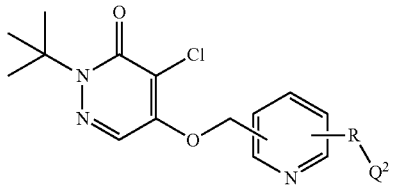

(2-0)

$Q^2$ is a removable substituent (a substituted sulfonyloxy group, a halogen atom, a hydroxy group, or the like).

Examples of the substituted sulfonyloxy group include a tosyloxy group (—OTs), a methanesulfonyloxy group (—OMs), a trifluoromethane sulfonyloxy group (—OTf), and a nitrobenzene sulfonyloxy group (—ONs). —OTs may be used as the substituted sulfonyloxy group.

Examples of the halogen atom include fluorine, chlorine, bromine, and iodine.

A compound represented by formula (2-0') (hereinafter, also referred to as compound (2-0')) is a precursor of the compound (1-0').

[Chemical formula 8]

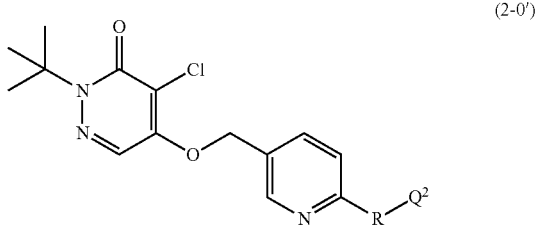

(2-0')

A compound represented by formula (2) (hereinafter, also referred to as compound (2)) is a precursor of the compound (1).

[Chemical formula 9]

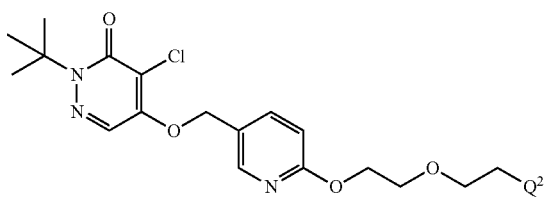

(2)

A compound represented by formula (2-2) is a precursor of the compound (1-2).

[Chemical formula 10]

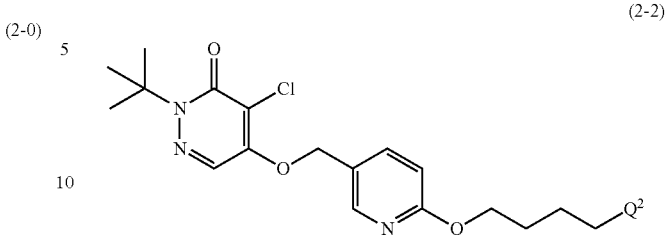

(2-2)

(Method for Synthesizing Precursor)

A compound (2-0) in which R is —$CH_2O(CH_2)_n$—, n is 2, and $Q^2$ is a hydroxy group can be synthesized from a known compound. For example, the compound (2-0) can be synthesized through synthesis schemes (steps 1 to 10) described in Experiment 2 in Examples described later. A compound (2-0) in which R is —$CH_2O(CH_2)_nOC_2H_4$— and $Q^2$ is a hydroxy group can be synthesized by referring to the synthesis schemes (steps 1 to 10) described in Experiment 2 in Examples described later and a synthesis scheme (c) described later.

A compound (2) in which $Q^2$ is a hydroxy group can be synthesized from a known compound. For example, the compound (2) can be synthesized through synthesis schemes (a) to (h) described in Experiment 1 in Examples described later.

A compound (2) in which $Q^2$ is a tosyloxy group can be synthesized from a known compound. For example, the compound (2) can be synthesized from the compound (2) in which $Q^2$ is a hydroxy group through synthesis scheme (i) described in Examples described later.

A compound (1) in which $Q^1$ is F is manufactured from a compound (2) by fluorinating the compound (2). For example, when $Q^2$ is —OTs, the method for fluorinating the compound (2) is indicated by synthesis scheme (A) below. When $Q^2$ is another substituted sulfonyloxy group or a halogen atom, a corresponding compound (1) can be synthesized by a similar synthesis scheme.

[Chemical formula 11]

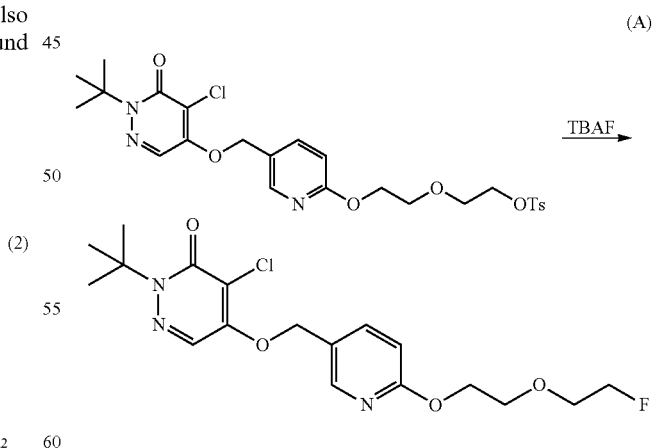

(A)

A compound (1) in which $Q^1$ is $^{18}F$ is manufactured from a compound (2) by [$^{18}F$] fluorinating the compound (2). For example, when $Q^2$ is —OTs, the method for [$^{18}F$] fluorinating the compound (2) is indicated by synthesis scheme (B) below. When $Q^2$ is another substituted sulfonyloxy group or a halogen atom, a corresponding compound (1) can be synthesized by a similar synthesis scheme.

[Chemical formula 12]

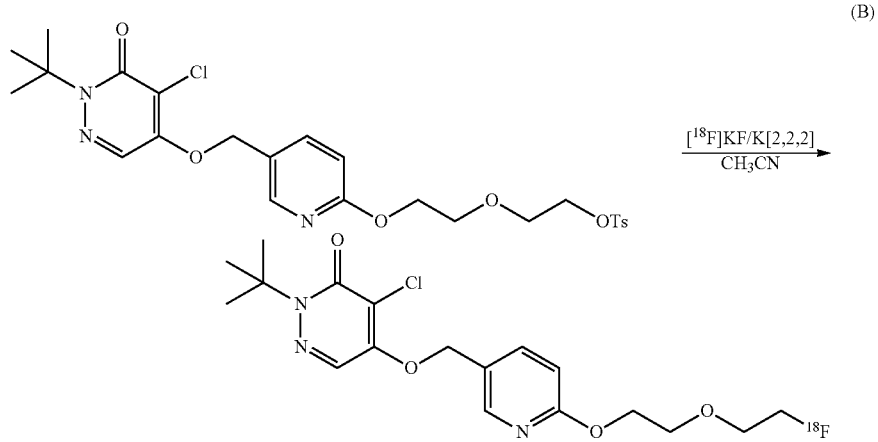

(B)

As a method for [$^{18}$F] fluorinating the compound (2), the compound. (2) can be [$^{18}$F] fluorinated by making the compound (2) react with a complex of a macrocyclic ligand and [$^{18}$F]KF in a solvent.

The solvent used during [$^{18}$F] fluorination is not particularly limited as long as the solvent can dissolve a starting material to some extent, and examples thereof include acetonitrile, dimethyl formamide (DMF), and dimethyl sulfoxide (DMSO). As the solvent, acetonitrile may be used.

Examples of the macrocyclic ligand include 4,7,13,16,21, 24-hexaoxa-1,10-diazabicyclo[8.8.8]hexacosane (K[2.2.2]), and 1,4,7,10,13,16-hexaoxa cyclooctadecane (18-crown-6). As the macrocyclic ligand, K[2.2.2] may be used.

For example, a method for manufacturing a compound (1) in which $Q^1$ is —OCH$_3$ from a compound (2) in which $Q^2$ is a hydroxy group is indicated by synthesis scheme (C) below.

[Chemical formula 13]

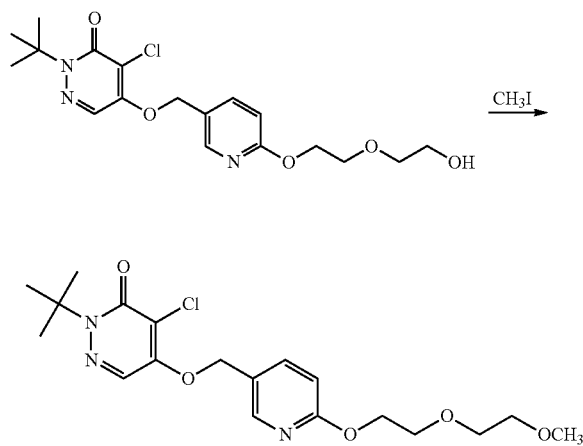

(C)

For example, a method for manufacturing the compound (1) in which $Q^1$ is —O$^{11}$CH$_3$ from the compound (2) in which $Q^2$ is a hydroxy group is indicated by synthesis scheme (D) below.

[Chemical formula 14]

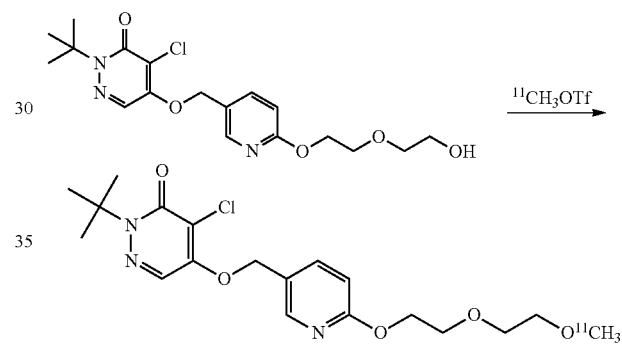

(D)

In synthesis scheme (D) above, $^{11}$CH$_3$OTf can be synthesized by a known method. For example, $^{11}$CH$_3$OTf can be synthesized through reaction formula (E).

[Chemical formula 15]

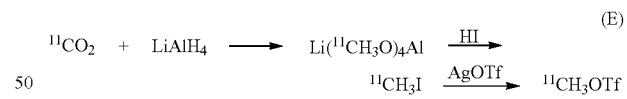

(E)

The compound (1-0) is suitable for detecting mitochondria Complex-1. For example, when a fluorescent dye or the like is bonded to the compound (1-0) or a positron-labeling is performed to the compound (1-0), the compound (1-0) can be used as labeled compound for mitochondria Complex-1. Particularly when $Q^1$ of the compound (1-0) is —O$^{11}$CH$_3$ or $^{18}$F, the compound (1-0) can emit a positron. A positron emitted from the compound (1-0) is bonded to an electron immediately and emits a γ-ray. By measuring this γ ray with an apparatus used for the PET method, biodistribution of the compound (1-0) can be imaged quantitatively with time.

Therefore, the diagnostic agent containing the compound (1-0) can specifically detect a cancer cell undergoing apoptosis as a "positive image" with high sensitivity. The present inventors consider a reason why the diagnostic agent can specifically detect a cancer cell undergoing apoptosis as follows. The reason is not limited thereto.

That is, the compound represented by formula (1-0) is suitable for detecting mitochondria Complex-1 (MC-1) as clarified in Examples described later. A cancer cell produces adenosine triphosphate (APT) necessary for living not using an electron transport system used by a normal cell (electron transport system involving MC-1) but using an anaerobic glycolysis system. Therefore, the compound is not bonded to MC-1 having a reduced function in a cancer cell, and a living cancer cell is measured as a "negative image" (image of a portion in which a probe is not present). On the other hand, in a cancer cell in which a gene or the like is broken by a cancer therapy such as a radiation therapy, metabolism is largely changed, and the electron transport system involving MC-1 is activated. Therefore, the compound is bonded to MC-1 in the cancer cell in which the electron transport system involving MC-1 is activated, and the cancer cell can be measured as a "positive image" (image of a portion in which a probe is present). Here, in the cancer cell in which the electron transport system involving MC-1 is activated, a large amount of active oxygen radicals are generated. However, the cancer cell has a lower enzyme activity to remove the radicals than a normal cell, and therefore disorder is caused in a DNA chain or lipid in a cell membrane by the radicals. As a result, apoptosis is induced and the cancer dies soon. That is, the compound can specifically detect a cancer cell undergoing apoptosis as a "positive image" with high sensitivity.

For example, the diagnostic agent can be manufactured by dissolving the compound (1-0) in any buffer solution. In this case, the diagnostic agent is provided as a solution, and may contain another component such as a surfactant, a preservative, or a stabilizer, in addition to the buffer component.

A method for diagnosing a therapeutic effect on cancer according to the present embodiment includes a step of performing a cancer therapy to a subject contracting cancer, a step of administering a compound represented by formula (1-0) to the subject, a step of detecting the compound in the cancer, and a step of analyzing an accumulation amount of the compound in the cancer quantitatively.

As described above, the diagnostic agent can specifically detect a cancer cell undergoing apoptosis as a "positive image" with high sensitivity. Therefore, a therapeutic effect on cancer can be diagnosed at an early stage after starting of a cancer therapy by the method.

The cancer is not particularly limited, but examples thereof include lung cancer, esophageal cancer, breast cancer, stomach cancer, liver cancer, gallbladder/bile duct cancer, pancreatic cancer, colon cancer, rectal cancer, bladder cancer, prostate cancer, uterine cancer, and skin cancer.

Examples of the subject include a human, a monkey, a mouse, and a rat, but are not limited thereto.

The method for a cancer therapy is not particularly limited as long as apoptosis in a target cancer cell can be induced by activation of the electron transport system involving MC-1. Examples of the method for a cancer therapy include a radiation therapy and chemotherapy. Examples of radiation used for the radiation therapy include an X-ray, an electron ray, and a γ ray. Examples of a chemical agent used in chemotherapy include a cancer molecular target drug such as dacarbazine, cisplatin, adriamycin, vinblastine, taxol, mitomycin, or an antibody drug.

A method for administering the compound to the subject may be any method as long as the compound (1-0) can reach a cancer cell, but is usually intravenous administration.

The time when the compound is administered to the subject may be any time after a cancer therapy is performed, but for example, may be administered at such an early stage as two to ten days after the cancer therapy is started.

The administration amount of the compound depends on a subject of administration and a method for detecting the compound, but is not particularly limited as long as the amount is sufficient for detecting the compound in a living body. For example, when a therapeutic effect on cancer is diagnosed using the diagnostic agent containing a compound (1-0) in which $Q^1$ is $^{18}F$ or $-O^{11}CH_3$ in formula (1-0), the administration amount of the compound (also referred to as "administration radiation dose") may be from 1 MBq/kg body weight to 1000 MBq/kg body weight. The compound may have a specific radioactivity of 10 to 10000 GBq/μmol.

When a therapeutic effect on cancer is diagnosed using the diagnostic agent by the PET method, the administration radiation dose of the diagnostic agent depends on sensitivity of a PET camera used and a volume of a subject individual. About 200 to 500 MBq/kg body weight is administered to a rodent (mouse, rat) as 0.1 to 0.5 mL of physiological saline solution. 40 to 200 MBq/kg body weight is administered to a non-human primate (monkey) as 0.5 to 2 mL of physiological saline. 2 to 10 MBq/kg body weight is administered to a human as 1 to 5 mL of a physiological saline solution.

The method for detecting the compound in cancer is not particularly limited, but can be performed according to a known method. For example, when the diagnostic agent containing a compound (1-0) in which $Q^1$ is $^{18}F$ or $-O^{11}CH_3$ in formula (1-0), the compound can be detected by the PET method. As a method of PET measurement, dynamic measurement may be performed for 60 minutes immediately after the diagnostic agent is administered, or PET measurement may be performed for 10 to 20 minutes after a probe is sufficiently accumulated in a cancer cell 30 to 40 minutes after the diagnostic agent is administered.

The method for analyzing an accumulation amount of the compound in the cancer quantitatively is not particularly limited, but can be performed according to a known method. Examples of the method include the following method. First, the probe-accumulated image obtained by the PET method and a form image of cancer obtained by CT measurement or the like are superimposed to identify a PET image of a cancer tissue. Subsequently, an interest region is set on the PET image of the cancer tissue, and a value normalized with a body weight of an individual as a subject and an administration radiation dose is used as an accumulation amount of the compound in the cancer tissue.

EXAMPLES

Hereinafter, the present invention will be described in more detail using Examples. However, the present invention is not limited to these Examples.

In the following Examples, unless otherwise specified, silica gel used for silica gel column chromatography was Silica Gel 60N (for flash chromatography) 40 to 50 μm manufactured by Kanto Chemical Co., Inc.

Experiment 1

Synthesis of BCPP-EF

BCPP-EF was synthesized according to the following steps 1 to 10. Hereinafter, each step will be described.

Step 1
A compound 3 was synthesized according to synthesis scheme (a).

[Chemical formula 16]

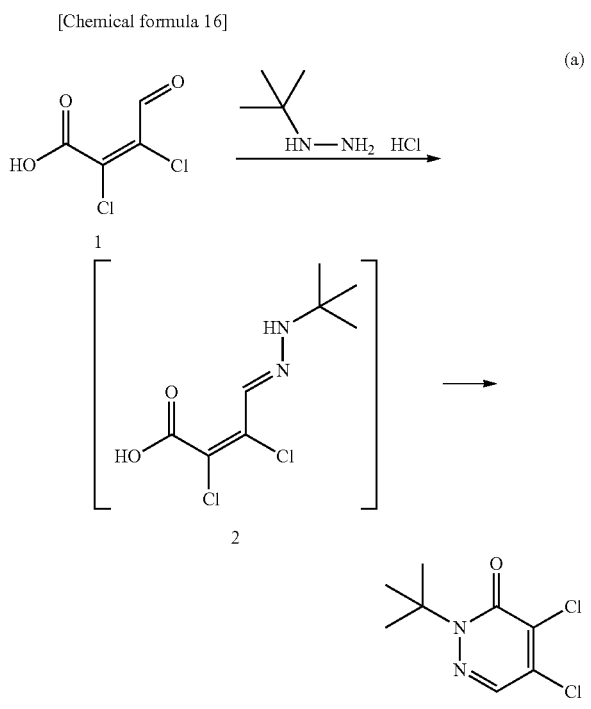

Mucochloric acid 1 (50 g, 0.29 mol) was dissolved in water (440 mL), and sodium carbonate (15.3 g, 0.14 mol) was added thereto. Tert-butyl hydrazine hydrochloride (36.9 g, 0.29 mol) was added to the solution at 0° C. The resulting reaction solution was stirred for 2.5 hours. The precipitated solid was filtered and washed with cold water, and then the solid precipitated under reduced pressure was dried to obtain an intermediate 2.

Acetic acid (500 mL) was added to the intermediate 2, and the reaction solution was refluxed for 30 minutes. Acetic acid in the reaction solution was distilled off under reduced pressure, and then was separated with methylene chloride and a sodium bicarbonate aqueous solution. The organic layer was washed with water, then dried over anhydrous magnesium sulfate, and concentrated under reduced pressure. The concentrated residue was purified by silica gel chromatography (heptane:chloroform=7:3 to 0:10) to obtain the light yellow solid compound 3 (52.9 g, yield: 80%).

Step 2
A compound 4 was synthesized according to synthesis scheme (b).

[Chemical formula 17]

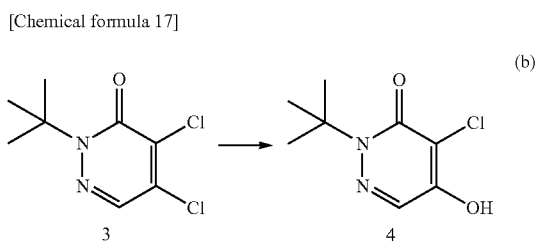

A potassium hydroxide (1.5 g, 27 mmol) aqueous solution (15 mL) was added to a 1,4-dioxane solution of the compound 3 (2 g, 9 mmol), and the mixed solution was refluxed for five hours. The resulting mixed solution was poured into ice water, concentrated hydrochloric acid was added thereto, and the precipitated solid (crude product) was collected by filtration. The crude product was washed with water and heptane in this order to obtain the compound 4 (1.6 g, yield: 91%).

Step 3
A compound 6 was synthesized according to synthesis scheme (c).

[Chemical formula 18]

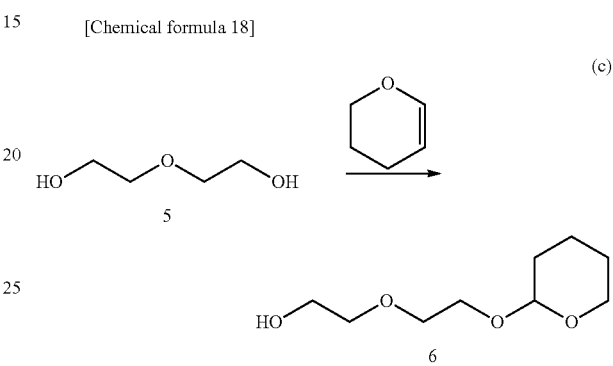

To a mixed solution of THF (40 mL) of diethylene glycol (22.8 mL, 0.24 mol) and 3,4-dihydro-2H-pyran (21.7 mL, 0.24 mol), and methylene chloride (400 mL), p-toluenesulphonic acid monohydrate (4.57 g, 24 mmol) was added at −10° C., and the reaction solution was stirred for one hour. Water was added to the reaction solution, and the mixture was separated with ether. The organic layer was washed with saturated saline, and dried over anhydrous sodium sulfate. Thereafter, the organic layer was concentrated under reduced pressure. The concentrated residue was purified by silica gel chromatography (heptane:ethyl acetate=50:50 to 0:100) to obtain the colorless liquid compound 6 (14 g, yield: 31%).

Step 4
A compound 9 was synthesized according to synthesis scheme (d).

[Chemical formula 19]

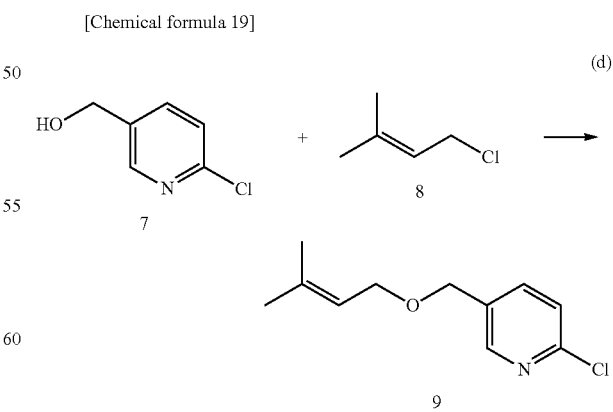

A DMF solution (30 mL) of 6-chloro-3-pyridine methanol 7 (5 g, 34.8 mmol) was slowly added to sodium hydride (1.51 g, 37.8 mmol (60% in oil)) in an argon atmosphere at 0° C. Thereafter, 1-chloro-3-methyl-2-butene 8 (4.11 mL, 36.5 mmol) was further added to the reaction solution, and the reaction solution was stirred at 25° C. for one hour. To the remaining raw material, 1-chloro-3-methyl-2-butene (2.0 mL, 17.7 mmol) was further added, and the reaction solution was stirred at 50° C. for one hour.

To the remaining raw material, sodium hydride (1.51 g, 37.8 mmol (60% in oil)) and 1-chloro-3-methyl-2-butene (8.0 mL, 71.1 mmol) were added, and the reaction solution was stirred at 50° C. for 30 minutes. Water was added to the reaction solution, and the mixture was separated with ethyl acetate. The organic layer was washed with saturated saline, and dried over anhydrous sodium sulfate. Thereafter, the organic layer was concentrated under reduced pressure. The concentrated residue was purified by silica gel chromatography (heptane:ethyl acetate=95:5 to 85:15) to obtain the colorless liquid compound 9 (7.0 g, yield: 96%).

Step 5

A compound 10 was synthesized according to synthesis scheme (e).

[Chemical formula 20]

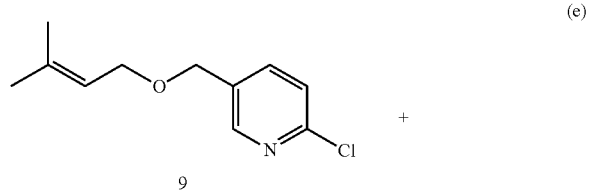

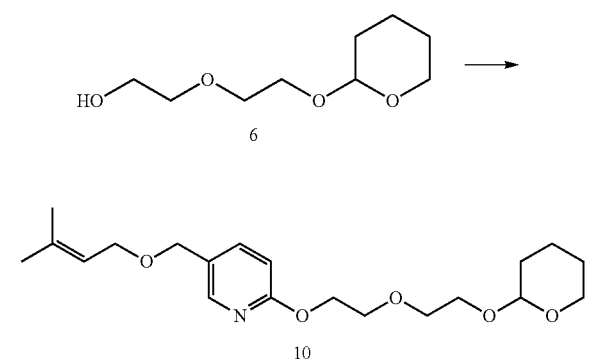

A 1,4-dioxane solution (8 mL) of the compound 6 (1.90 g, 10 mmol) was slowly added to sodium hydride (320 mg, 8 mmol (60% in oil)) in an argon atmosphere at 0° C., and the reaction solution was stirred at 60° C. for 30 minutes. Thereafter, a 1,4-dioxane solution (4 mL) of the compound 9 (0.84 g, 4 mmol) was added to the reaction solution, and the reaction solution was stirred at 170° C. for 30 minutes using a microwave. The reaction solution was cooled, then a saturated ammonium chloride aqueous solution was added to the reaction solution, and the mixture was separated with chloroform. The organic layer was washed with water and saturated saline, and dried over anhydrous magnesium sulfate. Thereafter, the organic layer was concentrated under reduced pressure. The concentrated residue was purified by silica gel chromatography (heptane:ethyl acetate =95:5 to 85:15) to obtain a compound 10 (4.9 g, yield: 96%).

Step 6

A compound 11 was synthesized according to synthesis scheme

[Chemical formula 21]

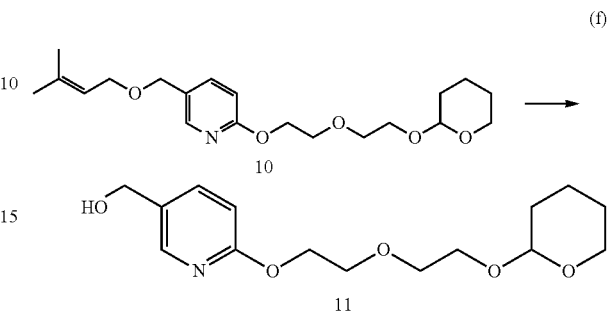

The compound 10 (5 g, 13.6 mmol) was slowly added to a DMSO solution (130 mL) of potassium tert-butoxide (15.3 g, 0.13 mol) in an argon atmosphere, and the reaction solution was stirred at 60° C. for 40 minutes. The reaction solution was cooled, then a saturated ammonium chloride aqueous solution was added to the reaction solution, and the mixture was separated with ethyl acetate. The organic layer was washed with water and saturated saline, and dried over anhydrous magnesium sulfate. Thereafter, the organic layer was concentrated under reduced pressure. The concentrated residue was purified by silica gel chromatography (heptane:ethyl acetate=80:20) to obtain the light yellow liquid compound 11 (2.7 g, yield: 68%).

Step 7

A compound 12 was synthesized according to synthesis scheme (g).

[Chemical formula 22]

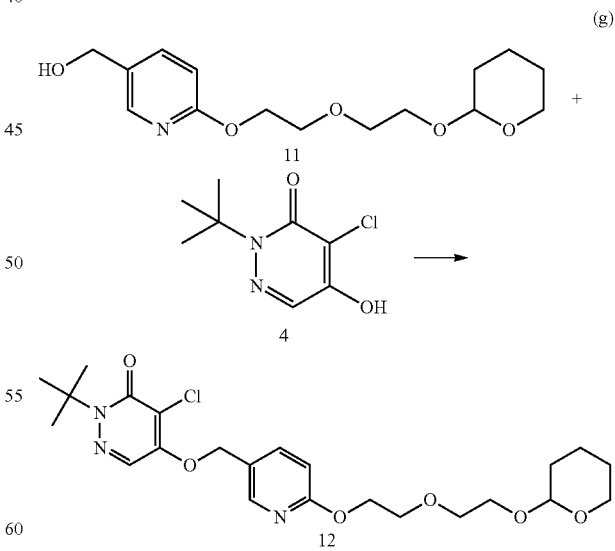

Diisopropyl azodicarboxylate (2.09 mL, 10.6 mmol) was added to a THF solution (100 mL) of the compound 4 (1.43 g, 7.04 mmol), the compound 11 (2.3 g, 7.74 mmol), and triphenylphosphine (2.77 g, 10.6 mmol), and the reaction solution was stirred at 25° C. for 16 hours. Water was added to the reaction solution, and the mixture was separated with ethyl acetate. The organic layer was washed with saturated saline, and dried over anhydrous magnesium sulfate. Thereafter, the organic layer was concentrated under reduced pressure. The concentrated residue was purified by silica gel chromatography (first time: heptane:ethyl acetate=90:10 to 60:40, second time: chloroform:methanol=99:1) to obtain the compound 12 (2.7 g, yield: 80%).

Step 8

A compound 13 was synthesized according to synthesis scheme (h).

[Chemical formula 23]

(h)

To a methanol solution (1 mL) of the compound 12 (96 mg, 7.2 mmol), p-toluenesulfonic acid monohydrate (2 mg, 0.01 mmol) was added, and the reaction solution was stirred at 25° C. for 16 hours. The reaction solution was concentrated under reduced pressure, and then the concentrated residue was purified by silica gel chromatography (heptane: ethyl acetate=70:30 to 20:80) to obtain the colorless solid compound 13 (96.9 mg, yield: 99%).

Step 9

A compound 14 was synthesized according to synthesis scheme (i).

[Chemical formula 24]

(i)

To a methylene chloride solution (10 mL) of the compound 13 (450 mg, 1.13 mmol), triethylamine (1.58 mL, 11.3 mmol), and 4-dimethylaminopyridine (13.8 mg, 0.11 mmol), p-toluenesulfonyl chloride (0.32 g, 1.69 mmol) was added at −10° C. or lower, and the reaction solution was stirred for 16 hours. Water was added to the reaction solution, and a target compound was extracted with methylene chloride twice. The organic layer was washed with saturated saline, and dried over anhydrous magnesium sulfate. Thereafter, the organic layer was concentrated under reduced pressure. The concentrated residue was purified by silica gel chromatography (heptane:ethyl acetate=90:10 to 40:60) to obtain the compound 14 (610 mg, yield: 97%).

Step 10

A compound 15 (BCPP-EF) was synthesized according to synthesis scheme (j).

[Chemical formula 25]

(j)

-continued

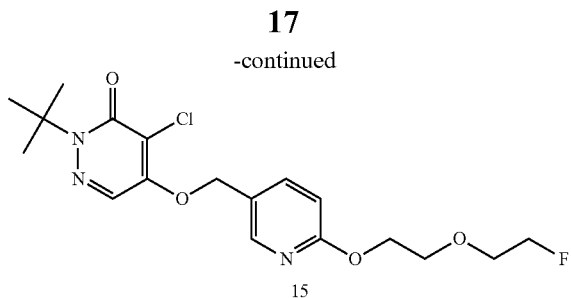

15

A mixed solution of the compound 14 (110 mg, 0.2 mmol) and tetrabutylammonium fluoride (0.6 mL, 0.6 mmol (1.0 mol/L in THF)) was stirred at 25° C. for 16 hours. The reaction solution was concentrated under reduced pressure, and then the concentrated residue was purified by silica gel chromatography (heptane:ethyl acetate=90:10 to 50:50) to obtain the compound 15 (BCPP-EF) (70 mg, yield: 88%).

Synthesis of BCPP-EM

BCPP-EM was synthesized according to the above steps 1 to 8 and the following step 11. Hereinafter, step 11 will be described.

Step 11

A compound 16 was synthesized according to synthesis scheme (k).

-continued

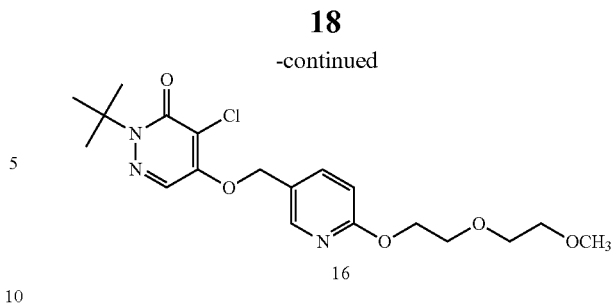

16

A 1,4-dioxane solution (2 mL) of the compound 13 (80 mg, 0.2 mmol) was added to sodium hydride (12 mg, 0.3 mmol (60% in oil)) in an argon atmosphere at 0° C. Thereafter, methyl iodide (125 µL, 2 mmol) was added to the reaction solution, and the reaction solution was stirred in a sealed tube at 25° C. for one hour. The reaction solution was cooled, then water was added to the reaction solution, and the mixture was separated with ethyl acetate. The organic layer was washed with saturated saline, and dried over anhydrous magnesium sulfate. Thereafter, the organic layer was concentrated under reduced pressure. The concentrated residue was purified by silica gel chromatography (heptane: ethyl acetate=70:30 to 30:70) to obtain the compound 16 (62 mg, yield: 75%).

Synthesis of [$^{18}$F]BCPP-EF

[$^{18}$F]BCPP-EF (compound 17) was synthesized according to the above steps 1 to 9 and the following synthesis scheme (1).

[Chemical formula 27]

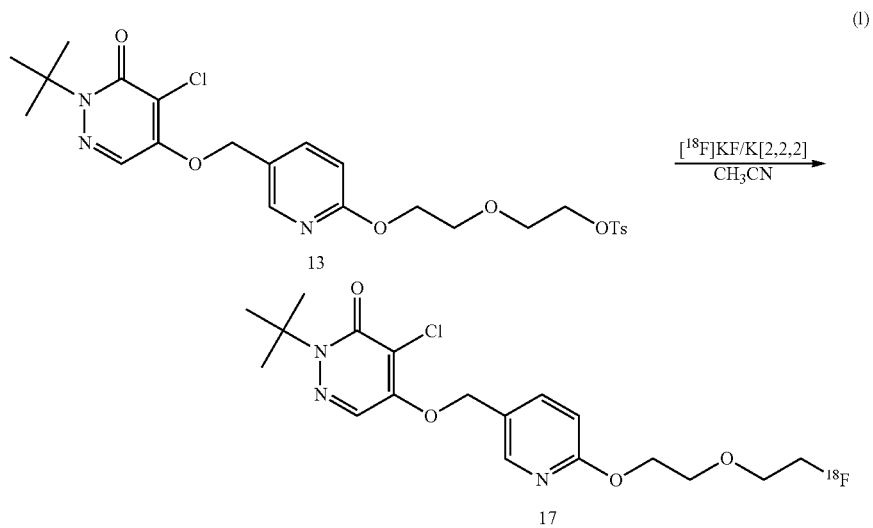

[Chemical formula 26]

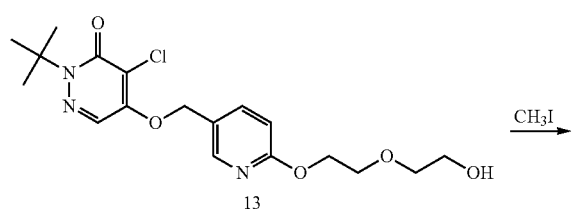

Labeling synthesis was performed using a [$^{18}$F] labeled compound automated synthesizer (F-110, F-120, Sumitomo Heavy Industries, Ltd., Tokyo). [$^{18}$F]F$^-$ collected from the target and trapped in an anion exchange resin AG1-X8 (Bio-Rad Laboratories, Hercules, USA) was desorbed with a 40 mM K$_2$CO$_3$ aqueous solution (0.5 mL, 20 µmol. A CH$_3$CN (Aldrich, St. Louis, Mo., USA) solution (2 mL) of K[2,2,2] (Merck, Darmstadt, Germany) (15 mg, 20 µmol) was added to the resulting solution, and the reaction solution was azeotropically dehydrated under a stream of He. CH$_3$CN (1 mL) was added to the residue, and azeotropic dehydration was repeated twice to prepare [$^{18}$F]KF/K[2,2,2] from which moisture had been removed. A CH$_3$CN (Sigma-Aldrich, St. Louis, USA) solution (1.5 mL) of a precursor (compound 14, 6.29 mg, 11.3 µmol) was added to [$^{18}$F]KF/

K[2,2,2], and fluorination was performed at 80° C. for 10 minutes. A mixed solution of $CH_3CN$ and $H_2O$ ($CH_3CN$: $H_2O$=3:7, 1.5 mL) was added to the resulting reaction mixture, and the reaction was stopped. Thereafter, the reaction solution was transferred to an HPLC injector. Furthermore, the reactor was rinsed with a mixed solution of $CH_3CN$ and $H_2O$ ($CH_3CN$: $H_2O$=3:7, 1.5 mL), and the mixed solution was transferred to the HPLC injector similarly. The crude product was purified by HPLC [column: Inertsil ODS-3 (5μ, 10.0×250 mm, GL Sciences Inc., Tokyo), mobile phase: $CH_3CN$:$H_2O$=500:500, flow rate: 6 mL/min, wavelength: 254 nm]. A radioactivity peak at a retention time of 17.4 minutes was fractionated. The fractionated solution was concentrated and dried with an evaporator. Thereafter, the product concentrated and dried was dissolved again in a 0.1% Tween80/physiological saline (5 mL), and [$^{18}$F]BCPP-EF (2.36 GBq) was collected.

A part of the product was extracted and analyzed by HPLC [column: Finepak SIL C18S (5μ, 4.6×150 mm, JASCO CORPORATION, Tokyo), mobile phase: $CH_3CN$: 30 mM $CH_3ONH_4$:$CH_3COOH$=500:500:2, flow rate: 2 mL/min, wavelength: 254 nm]. The radiochemical yield, specific radioactivity, and radiochemical purity were 16.98% (decay corrected), 84.3 GBq/μmol, and 100%, respectively. Total synthesis time was about 63 minutes from the time of irradiation end (End of bombardment, EOB).

When [$^{18}$]BCPP-EF was synthesized with 3.54 mg of a precursor (compound 14), the radiochemical yield was 4.02%. The radiochemical yield was improved to 16.98% by increasing the precursor to 6.29 mg. The radiochemical purity of the resulting final product and the specific radioactivity were 100% and 84.3 GBq/μmol, respectively. It was possible to obtain a purity and an yield sufficient for PET experiments.

Synthesis of [$^{11}$C]BCPP-EM

[$^{11}$C]BCPP-EM was synthesized according to the above steps 1 to 8 and the following synthesis scheme (m).

[Chemical formula 28]

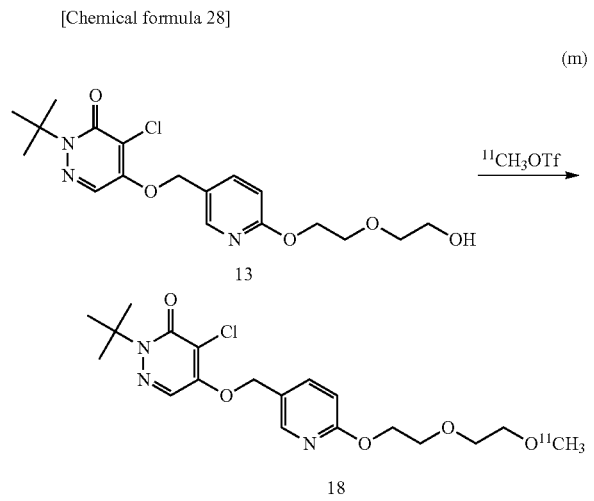

(m)

A proton was accelerated to 18 MeV by a cyclotron (HM-18, Sumitomo Heavy Industries, Ltd., Tokyo). On the other hand, target gas in which pure nitrogen gas (G grade, Japan Fine Products, Kanagawa) had been encapsulated at a pressure of about 17 kg/cm² was prepared. The target gas was irradiated with the proton at a current value of about 20 μA, and [$^{11}$C] was manufactured by a $^{14}$N(p,α)$^{11}$C nuclear reaction. [$^{11}$C] was present in a chemical form of [$^{11}$C]$CO_2$ in the target gas. The target gas containing [$^{11}$C]$CO_2$ was introduced into a cooled 0.1 M LiAlH$_4$/tetrahydrofuran (THF) solution (500 μL) (ABX Advanced Biochemical Compounds, Germany) with an automatic synthesis device (Sumitomo Heavy Industries, Ltd., Tokyo). At this time, the flow rate of the target gas was 400 mL/min. After the target gas was introduced, the resulting reaction solution was bubbled through nitrogen gas (gas flow rate, 200 mL/min), and was heated to 200° C. to distill off THF. After THF was distilled off, the reactor was cooled once, and hydriodic acid (Nacalai Tesque, Inc., Kyoto, 0.5 ml) was added to the reaction solution and was heated to 150° C. The produced [$^{11}$C]methyl iodide was distilled and allowed to pass through an AgOTf (Sigma Aldrich, USA) column heated to 200° C. to obtain [$^{11}$C]methyl triflate. The [$^{11}$C]methyl triflate which had passed through the column was introduced into a solution of a precursor (compound 13) immediately.

The precursor (compound 13, 2 mg) was dissolved in 2-butanone (Wako Pure Chemical Industries, Ltd., Tokyo, 0.3 mL). NaH (about 2 mg) was added to the resulting precursor solution for preparation. The [$^{11}$C]methyl triflate obtained by distillation was introduced into the resulting precursor solution, and introduction of the [$^{11}$C]methyl triflate was stopped when the radioactivity reached equilibrium. Thereafter, a methylation reaction of the precursor was performed under the conditions of 40° C. and five minutes.

A [$^{11}$C]BCPP-EM solution was fractionated by high-performance liquid chromatography (stationary phase: Megapak SIL C18-10, 7.6×250 mm (JASCO CORPORATION, Tokyo), mobile phase: acetonitrile (Wako Pure Chemical Industries, Ltd., Osaka):30 mM ammonium acetate aqueous solution (Wako Pure Chemical Industries, Ltd., Osaka)=450:550, flow rate: 6 mL/min, wavelength: 254 nm). An eluent was distilled off from the fractionated solution with an evaporator (Sumitomo Heavy Industries, Ltd., Tokyo). Thereafter, a physiological saline solution (Otsuka Pharmaceutical, Co., Ltd., Tokyo) was added to the resulting residue to obtain a final formulation.

The radioactivity of the final formulation was measured (Aloka, Tokyo). A part of the final formulation was analyzed by high-performance liquid chromatography (stationary phase: Finepack C18-S, 4.6×150 mm (JASCO CORPORATION, Tokyo), mobile phase: acetonitrile (Wako Pure Chemical Industries, Ltd., Osaka):30 mM ammonium acetate (Nacalai Tesque, Inc., Kyoto):acetic acid (Wako Pure Chemical Industries, Ltd., Osaka)=500:500:2, flow rate: 2 mL/min, wavelength: 254 nm).

When the target gas was irradiated with the proton about for 60 minutes, the production amount of [$^{11}$C]BCPP-EM was from 0.26 to 2.01 GBq, and the radiochemical purity was 93.6% or more.

In the separation HPLC, the retention time of the precursor of [$^{11}$C]BCPP-EM (compound 13) was 5.2 minutes, and the retention time of [$^{11}$C]BCPP-EM was 10 minutes. In analytical HPLC, the retention time of [$^{11}$C]BCPP-EM was 4.0 minutes.

Experiment 2

Synthesis of BMS-P

BMS-P (compound 15″) was synthesized according to the following steps 1 to 12. Hereinafter, each step will be described.

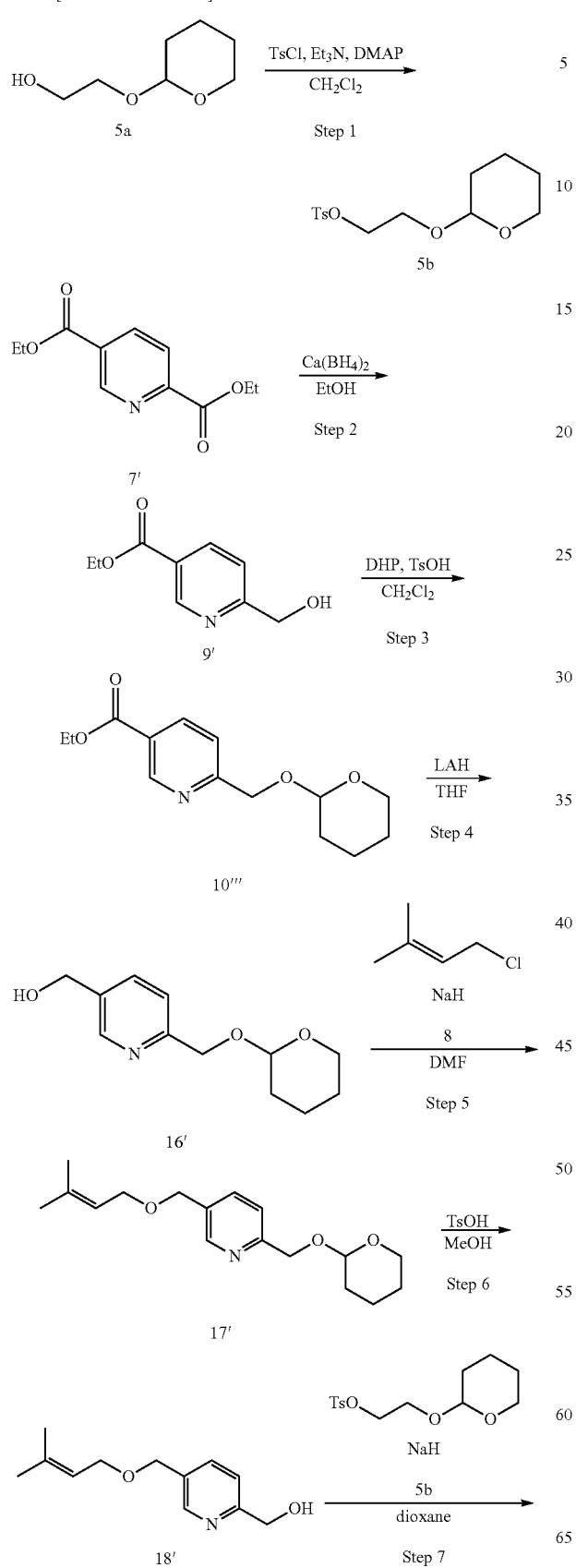
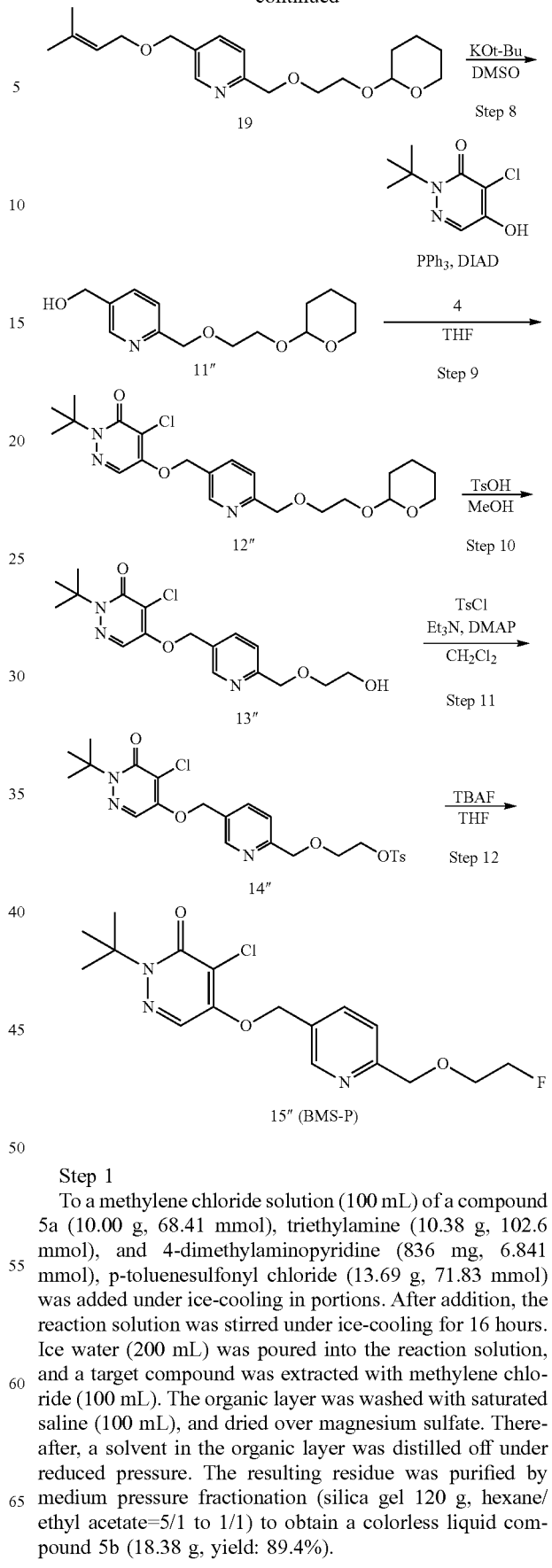

Step 1

To a methylene chloride solution (100 mL) of a compound 5a (10.00 g, 68.41 mmol), triethylamine (10.38 g, 102.6 mmol), and 4-dimethylaminopyridine (836 mg, 6.841 mmol), p-toluenesulfonyl chloride (13.69 g, 71.83 mmol) was added under ice-cooling in portions. After addition, the reaction solution was stirred under ice-cooling for 16 hours. Ice water (200 mL) was poured into the reaction solution, and a target compound was extracted with methylene chloride (100 mL). The organic layer was washed with saturated saline (100 mL), and dried over magnesium sulfate. Thereafter, a solvent in the organic layer was distilled off under reduced pressure. The resulting residue was purified by medium pressure fractionation (silica gel 120 g, hexane/ethyl acetate=5/1 to 1/1) to obtain a colorless liquid compound 5b (18.38 g, yield: 89.4%).

Step 2

Calcium chloride (29.92 g, 269.6 mmol), ethanol (390 mL), and THF (390 mL) were input into a reactor in an Ar atmosphere, and subsequently sodium borohydride (20.40 g, 539.2 mmol) was introduced into the reactor under ice-cooling in portions. After introduction of sodium borohydride, the reaction solution was stirred under ice-cooling for 2.5 hours. A compound 7' (30.09 g, 134.8 mmol) was introduced into the reaction solution under ice-cooling in portions, and the reaction solution was stirred under ice-cooling for 30 minutes. The reaction solution was poured into ice water (1.5 L), and then ammonium chloride (300 g) was added to the reaction solution while being stirred. A target compound was extracted with ethyl acetate (1 L×2). The organic layer was washed with water (1 L) and saturated saline (1 L) sequentially. The organic layer was dried over magnesium sulfate, and then a solvent in the organic layer was distilled off under reduced pressure to obtain a light yellowish brown solid compound 9'(16.12 g, yield: 66.0%).

Step 3

To a methylene chloride solution (500 mL) of the compound 9' (17.07 g, 94.21 mmol) and p-toluenesulphonic acid monohydrate (18.11 g, 94.21 mmol), 3,4-dihydro-2H-pyran (23.55 mL, 259.2 mmol) was added under ice-cooling, and the reaction solution was stirred for 18 hours. The organic layer was washed with saturated sodium bicarbonate water (500 mL) and saturated saline (500 mL) sequentially. The organic layer was dried over magnesium sulfate, and then a solvent in the organic layer was distilled off under reduced pressure to obtain a light yellowish brown liquid compound 10''' (42.72 g, crude yield: 170.9%). The compound 10''' was subjected to the subsequent step while the compound 10''' was crude.

Step 4

A THF solution (200 mL) of the crude compound 10''' (42.72 g, Net=24.99 g, 94.21 mmol) was dropwise added to a THF suspension solution (100 mL) of lithium aluminum hydride (7.988 g, 210.5 mmol) in an Ar atmosphere under ice-cooling. Thereafter, the reaction solution was stirred at room temperature for one hour. Water (8 mL), a 15% sodium hydroxide aqueous solution (8 mL), and water (24 mL) were dropwise added to the reaction solution sequentially under ice-cooling, and the reaction was stopped. The resulting mixture was filtered, and the slurry was washed with ethyl acetate (600 mL). The resulting filtrate was washed with saturated saline (300 mL), and dried over sodium sulfate. Thereafter, a solvent in the filtrate was distilled off under reduced pressure. The resulting residue was purified by medium pressure fractionation (silica gel 200 g, hexane/ethyl acetate=1/1 to ethyl acetate only (0/1)) to obtain a light yellowish brown liquid compound 16' (14.98 g, yield from compound 9': 71.2%).

Step 5

Sodium hydride (3.489 g, 87.22 mmol as a 60% conversion) was added in portions to a DMF solution (60 mL) of the compound 16' (14.98 g, 67.09 mmol) in an Ar atmosphere under ice cooling, and the reaction solution was stirred at room temperature for one hour. Subsequently, a compound 8 (10.53 g, 100.7 mmol) was added to the reaction solution, and stirred at 50° C. for three hours. Ice water (300 mL) was added to the reaction solution, and a target compound was extracted with ethyl acetate (300 mL). The organic layer was washed with water (300 mL) and saturated saline (300 mL) sequentially. The organic layer was dried over magnesium sulfate, and then a solvent in the organic layer was distilled off under reduced pressure. The resulting residue was purified by medium pressure fractionation (silica gel 200 g, hexane/ethyl acetate=10/1 to 1/1) to obtain a light yellowish brown liquid compound 17' (15.40 g, yield: 78.8%).

Step 6

To a methanol solution (154 mL) of the compound 17' (15.40 g, 52.85 mmol), p-toluenesulfonic acid monohydrate (502.7 mg, 2.643 mmol) was added, and the reaction solution was stirred at room temperature for 18 hours. Thereafter, the reaction solution was heated and refluxed for eight hours. The reaction solution was concentrated, and the resulting residue was purified by medium pressure fractionation (silica gel 200 g, hexane/ethyl acetate=1/1 to ethyl acetate only (0/1)) to obtain a light yellowish brown liquid compound 18' (10.78 g, yield: 98.4%).

Step 7

Sodium hydride (2.430 g, 60.74 mmol as a 60% conversion) was added in portions to a dioxane solution (100 mL) of the compound 18' (10.76 g, 51.91 mmol) in an Ar atmosphere under ice cooling, and the reaction solution was stirred at room temperature for 15 minutes. Subsequently, a dioxane solution (60 mL) of the compound 5b (18.24 g, 60.74 mmol) was added thereto, and the reaction solution was stirred at 50° C. for two hours. Ice water (300 mL) was added to the reaction solution, and a target compound was extracted with ethyl acetate (200 mL×2). The organic layer was washed with saturated saline (200 mL). The organic layer was dried over sodium sulfate, and then a solvent in the organic layer was distilled off under reduced pressure. The resulting residue was purified by medium pressure fractionation (silica gel 200 g, hexane/ethyl acetate=4/1 to ethyl acetate only (0/1)) to obtain a light yellowish brown liquid compound 19 (14.21 g, yield: 81.6%).

Step 8

Potassium t-butoxide (49.00 g, 436.7 mmol) was added to a DMSO solution (375 mL) of the compound 19 (14.21 g, 43.67 mmol) in an Ar atmosphere, and the reaction solution was stirred at 60° C. for 30 minutes. The reaction solution was poured into ice water (1 L), and a target compound was extracted with ethyl acetate (500 mL×4). The organic layer was washed with saturated saline (500 mL), and dried over sodium sulfate. Thereafter, a solvent in the organic layer was distilled off under reduced pressure. The resulting residue was purified by medium pressure fractionation (silica gel 200 g, hexane/ethyl acetate=1/1 to ethyl acetate only (0/1)) to obtain a light yellow liquid compound 11'' (4.201 g, yield: 37.1%).

Step 9

A THF solution (23 mL) of diisopropyl azodicarboxylate (DIAD, 4.768 g, 23.58 mmol) was dropwise added to a THF solution (200 mL) of the compound 4 (3.185 g, 15.72 mmol), the compound 11'' (4.201 g, 15.72 mmol), and triphenylphosphine (6.185 g, 23.58 mmol) in an Ar atmosphere under ice cooling, and the reaction solution was stirred at room temperature for 16 hours. The reaction solution was concentrated, and the resulting residue was purified by medium pressure fractionation (silica gel 200 g, hexane/ethyl acetate=4/1 to 1/1, twice) to obtain a slightly yellow liquid compound 12'' (431 mg, yield: 6.1%).

Step 10

To a methanol solution (4.3 mL) of the compound 12'' (430 mg, 0.9515 mmol), p-toluenesulfonic acid monohydrate (9.05 mg, 0.0457 mmol) was added, and the reaction solution was stirred at room temperature for 18 hours. The reaction solution was further stirred at 60° C. for four hours. The reaction solution was concentrated, and the resulting residue was purified by medium pressure fractionation (silica gel 60 g, hexane/ethyl acetate=3/1 to ethyl acetate only (0/1)) to obtain a colorless liquid compound 13" (242 mg, yield: 69.2%).

Step 11

To a methylene chloride solution (3 mL) of the compound 13" (140.6 mg, 0.3822 mmol), triethylamine (386.7 mg, 3.822 mmol), and 4-dimethylaminopyridine (4.67 mg, 0.03822 mmol), p-toluenesulfonyl chloride (109.3 mg, 0.5734 mmol) was added at −10° C. After p-toluenesulfonyl chloride was added, the reaction solution was stirred at −10° C. for 16 hours. Ice water (20 mL) was poured into the reaction solution, and a target compound was extracted with methylene chloride (20 mL). The organic layer was washed with saturated saline (10 mL), and dried over magnesium sulfate. Thereafter, a solvent in the organic layer was distilled off under reduced pressure to obtain a viscous red brown liquid compound 14" (201.2 mg, crude yield 100.8%). The compound 14" was subjected to the subsequent step while the compound 14" was crude.

Step 12

The crude compound 14" (195 mg, Net=193.5 mg, 0.3706 mmol) was dissolved in THF (2 mL), 1M TBAF/THF (2 mL) and TBAF.xH$_2$O (500 mg) were added thereto, and the reaction solution was stirred at room temperature for two hours. Ice water (50 mL) was poured into the reaction solution, and a target compound was extracted with ethyl acetate (50 mL) The organic layer was washed with saturated saline (20 mL), and dried over magnesium sulfate. Thereafter, a solvent in the organic layer was distilled off under reduced pressure. The resulting residue was purified by medium pressure fractionation (silica gel 60 g, hexane/ethyl acetate=4/1 to 1/1) to obtain the red brown liquid compound 15" (BMS-P) (47.6 mg, yield: 25.4%) together with a lot separately prepared and purified from the compound 13" (50 mg).

Evaluation of Binding Affinity with Respect to Mitochondria Complex-1.

A dose-response curve of each of a TEST substance and a positive substance was created, and a concentration (IC$_{50}$ value) at which the TEST substance and the positive substance suppress 50% of bonding between a tracer and mitochondrial Complex-1 (receptor) and an absolute inhibition constant (Ki) were calculated. As the TEST substance, [$^{18}$F]BMS-747158-02 (2-tert-butyl-4-chloro-5-[4-(2-fluoroethoxymethyl)-benzyloxy]-2H-pyridazin-3-one, hereinafter also referred to as "BMS"), BCPP-EF, BCPP-BF, BCPP-PF, BCPP-EM, and BMS-P were used. The details will be described below.

Preparation of Mitochondrial Fraction Stock Solution

An animal tissue was weighed (wet weight), a homogenization buffer solution (10 mmol/L Tris-HCl buffer solution (pH, 7.40) of 250 mmol/L sucrose, 1 mmol/L succinic acid, and 0.2 mmol/L EDTA) was added in an amount twice the amount of the animal tissue, and the mixture was homogenized under ice cooling. Thereafter, the homogenized suspension solution was centrifuged (1200×g, 4° C., 20 minutes). The supernatant was collected and centrifuged (26000×g, 4° C., 15 minutes). The residue precipitated was collected, and homogenized by adding a homogenization buffer solution so as to obtain a concentration of 100 mg tissue eq./mL. The resulting mitochondrial fraction stock solution was stored at −80° C. before use. The protein concentration of the mitochondrial fraction was measured using BCA Protein Assay Reagent (manufactured by Pierce Companies). A brain of a rat and a heart of a bull were used for the animal tissue.

Preparation of Mitochondrial Fraction Solution

By diluting the mitochondrial fraction stock solution with a buffer solution, a mitochondrial fraction solution having a concentration twice the final concentration was prepared (before use preparation). The final concentration of the mitochondrial fraction solution was 45 μg protein/mL.

Preparation of TEST Substance Solution

By diluting the TEST substance with DMSO in stages, a solution having a concentration 100 times the final concentration was prepared. Furthermore, by diluting the prepared solution having each concentration with Milli-Q water ten times, a TEST substance solution having a concentration 10 times the final concentration was prepared (prepared before use).

The final concentration of the TEST substance was in the following concentration range.

BMS; $3\times10^{-11}$ to $3\times10^{-8}$ mol/L
BCPP-EF; $1\times10^{-10}$ to $1\times10^{-7}$ mol/L
BCPP-BF; $3\times10^{-11}$ to $3\times10^{-8}$ mol/L
BCPP-PF; $1\times10^{-10}$ to $1\times10^{-7}$ mol/L
BCPP-EM; $3\times10^{-10}$ to $3\times10^{-7}$ mol/L
BMS-P; $1\times10^{-7}$ to $1\times10^{-4}$ mol/L.

Preparation of Positive Substance Solution

The positive substance was weighed and dissolved in DMSO. By diluting the resulting solution with DMSO in stages, a solution having a concentration 100 times the final concentration was prepared. Furthermore, by diluting the prepared solution having each concentration with Milli-Q water ten times, a positive substance solution having a concentration 10 times the final concentration was prepared (prepared before use). Rotenone was used as the positive substance. The final concentration of the positive substance was from $3\times10^{-11}$ to $3\times10^{-8}$ mol/L.

Preparation of Substitution Substance Solution

By weighing a substitution substance and dissolving the substitution substance in DMSO, a solution having a concentration 100 times the final concentration was prepared. Furthermore, by diluting the prepared solution with Milli-Q water ten times, a substitution substance solution having a concentration ten times the final concentration was prepared (prepared before use). Rotenone was used as the substitution substance. The final concentration of the substitution substance was $1\times10^{-5}$ mol/L.

Preparation of Tracer Solution

By diluting a tracer stock solution with a buffer solution, a tracer solution having a concentration ten times the final concentration was prepared (before use preparation). Dihydrorotenone[2-isopropyl-$^3$H(N)] was used as the tracer.

The final concentration of the tracer was 4.5 nmol/L at the first time, 4.4 nmol/L at the second time, and 4.5 nmol/L at the third time.

Measurement Procedure

Measurement was performed according to the following order. Two samples were prepared for each concentration, and each sample was measured three times.

1: To a tube used for calculating a non-specific bonding, 100 μL of the substitution substance solution was added (final concentration of DMSO: 1%). To a tube used for calculating a total bonding, 100 μL of 10% DMSO was added (final concentration of DMSO: 1%). To a tube used for calculating an inhibition ratio of the TEST substance or the positive substance, 100 μL of the TEST substance solution or the positive substance solution was added (final concentration of DMSO: 1%).

2: A buffer solution (300 μL) was added to each tube.

3: A tracer solution (100 μL) was added to each tube.

4: A mitochondrial fraction solution (500 μL) was added to each tube.

5: The reaction solution included in each tube was incubated at 22° C. for 30 minutes.

6: The reaction solution was filtered by a cell harvester (GF/C, Whatman), and the filter paper used for the filtration was washed with a 50 mmol/L Tris-HCl buffer solution (pH 7.40, 3 mL) three times.

7: The filter paper was transferred to a vial bottle for measurement, a liquid scintillator (PICO-FLUOR™ PLUS, 5 mL) was added thereto, and radiation dose was measured with a liquid scintillation counter (measurement time, two minutes).

Calculation of Inhibition Ratio

The inhibition ratio was calculated by a formula of "100-bonding ratio".

Bonding ratio: $[(B-N)/(B_0-N)] \times 100(\%)$

B: bonding radiation dose in the presence of TEST substance (individual value)

$B_0$: total bonding radiation dose in the absence of TEST substance (average value)

N: non-specific bonding radiation dose (average value)

By assuming the inhibition ratio to be 0% when the inhibition ratio was 0% or less and assuming the inhibition ratio to be 100% when the inhibition ratio was more than 100%, the inhibition ratio was calculated.

The inhibition ratio of the positive substance was calculated in a similar manner to that of the TEST substance.

Creation of Dose-Response Curve (Calculation of $IC_{50}$ Value)

The dose-response curve was created by performing logit conversion of a ratio $((B-N)/(B_0-N))$ between specific bonding radioactivity $(B-N)$ in the presence of a TEST substance and total bonding radioactivity $(B_0-N)$ in the absence of the TEST substance and then applying the obtained value to a logit-log model to plot the value against a common logarithm of the final concentration of the TEST substance.

The following regression formula was used for regression of the dose-response curve.

$$Y = aX + b$$

(Y=logit $y=\ln(y/(1-y))$, $y=(B-N)/(B_0-N)$)
(X=log x, x indicates a final concentration of a TEST substance.)
(a=constant, b=constant)

An $IC_{50}$ value was calculated from the obtained regression formula In the regression, inhibition ratios having an average beyond a range of 5% to 95% at the final concentration of the TEST substance were not employed, and the $IC_{50}$ value was calculated using inhibition ratios continuously increasing in the range.

Calculation of Ki Value

A Ki value of a TEST substance or a positive substance was calculated from the following formula using a tracer concentration used for the TEST for calculating the $IC_{50}$ value (L), an obtained $IC_{50}$ value, and a Kd value of the tracer, with respect to mitochondria Complex-1, obtained by a TEST of Scatchard analysis.

$$Ki = \frac{IC_{50}}{1 + \frac{L}{Kd}}$$ [Numerical formula 1]

The dose-response curve is illustrated in FIG. 1. It has been found that any TEST substance is bonded to mitochondria Complex-1 in a concentration-dependent manner. BCPP-BF indicates the lowest $IC_{50}$. It has been suggested that BCPP-BF has a high affinity with respect to mitochondria Complex-1. On the other hand, BMS-P indicates a higher $IC_{50}$ than the other TEST substances. It has been suggested that BMS-P is bonded to mitochondria Complex-1 with a low affinity.

Judgment of Effect of Cancer Therapy Using Mouse

Measurement of Tumor Volume

SCCVII cells ($1 \times 10^5/0.5$ mL) which were malignant tumors derived from epithelial cells of a rodent and had a high radiation sensitivity were implanted to a hind leg thigh of a female C3H/HeN mouse (8 weeks old) subcutaneously.

The tumor was measured regularly with calipers, and the tumor volume (Tvol) was calculated by the following formula.

$Tvol = \pi t l w h/6$ (mm$^3$) ($l$=longer diameter (mm), $w$=width (mm), $h$=height (mm))

Figure 2:
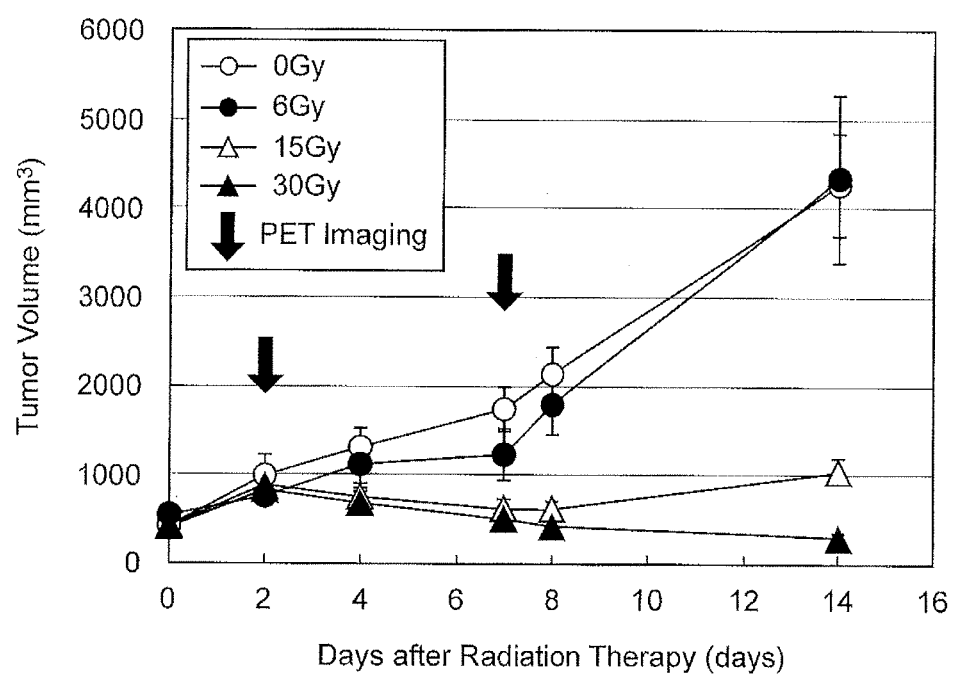
FIG. 2 is a graph illustrating change in tumor volume with time after a radiation therapy.

The tumor volume was measured for fourteen days after a cancer therapy using irradiation with an X-ray described below was started. The results are illustrated in FIG. 2.

Cancer Therapy Using Irradiation with X-Ray

When the tumor volume reached about 100 mm$^3$, a cancer therapy using irradiation with an X-ray was performed to a tumor site of a mouse at a dose ratio of 1.2 Gy/minute using an apparatus which can perform irradiation with an X-ray having an energy of 250 keV (Hitachi Power Solutions MBR-1520R-3). As conditions of irradiation with X-ray, four conditions of non-irradiation (0 Gy, control), 6 Gy, 15 Gy, and 30 Gy were set. Also after the irradiation treatment, the tumor volume was regularly measured according to the above method.

Judgment of Effect of Cancer Therapy Using PET Measurement

Figure 3:
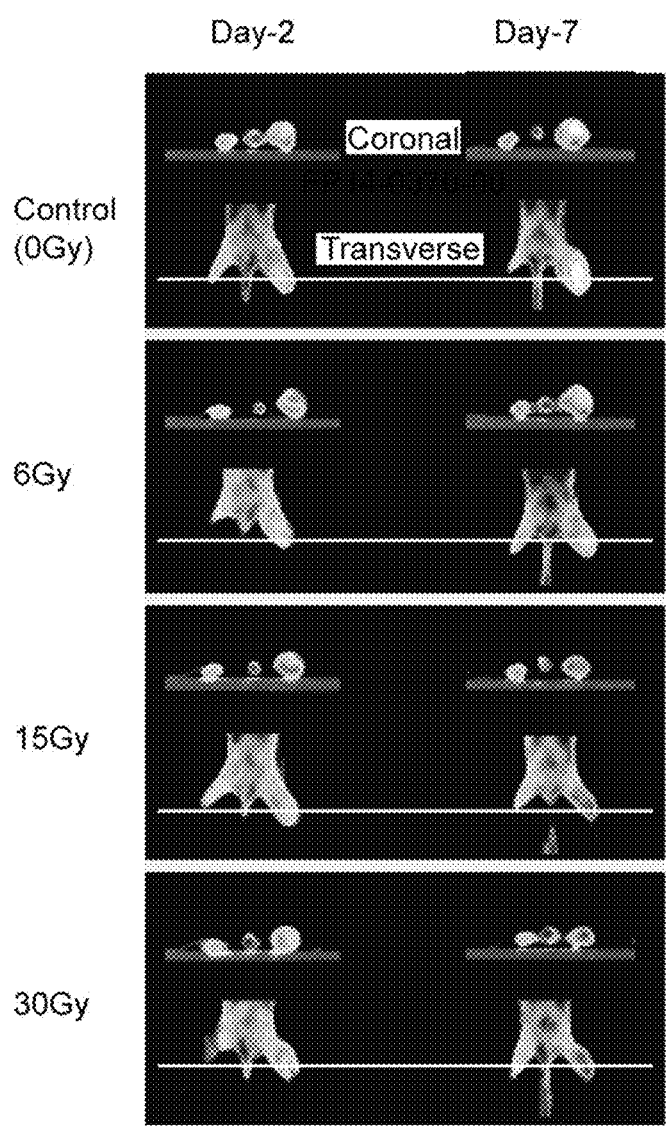
FIG. 3 is a PET image illustrating an effect of a radiation therapy in a tumor tissue of mice.

Two days and seven days after irradiation with X-ray, a mouse with a tumor tissue (cancer-bearing mouse) was anesthetized by isoflurane gas. Thereafter, four mice were fixed at one time in a gantry of an animal PET camera (HAMAMATSU SHR-38000). For absorption correction, transmission measurement was performed using a $^{68}$Ge-$^{68}$Ga calibration-ray source for 15 minutes. Thereafter, about 5 MBq/0.2 mL of [$^{18}$F]BCPP-EF was administered into a tail vein of a mouse, and dynamic emission measurement was performed for 60 minutes. FIG. 3 illustrates a PET image showing an effect of the radiation therapy in the tumor tissue of a mouse.

After the PET measurement was finished, each of the mice was moved to a small animal X-CT (SHIMADZ Clairvivo CT) with a fixed stand while being anesthetized, and CT measurement was performed for ten minutes. A form image (X-CT image) obtained by the CT measurement was collected, a PET accumulated image 40 to 60 minutes after administration of [$^{18}$F]BCPP-EF was superimposed on the X-CT image, and a PET image of a cancer tissue was identified.

Figure 4:
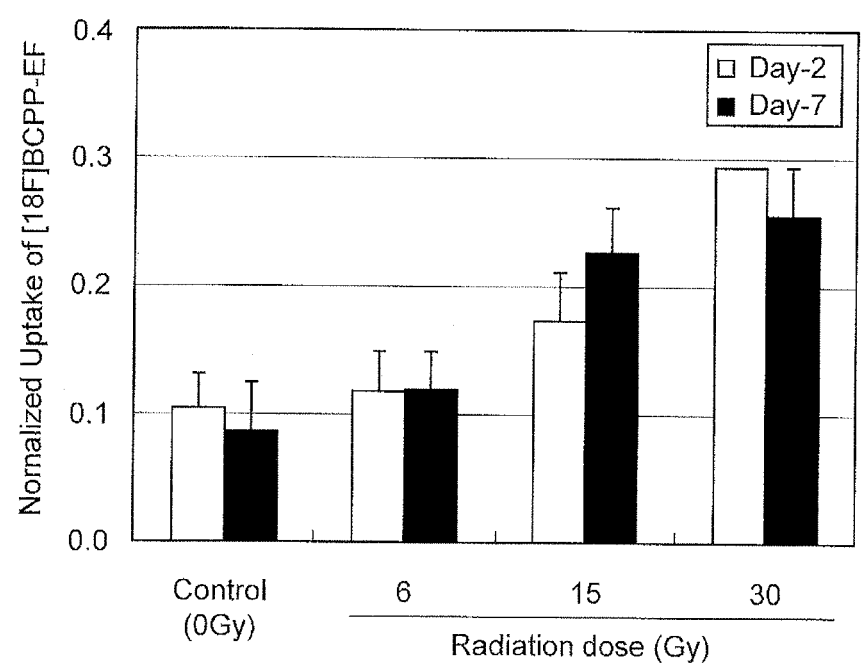
FIG. 4 is a graph illustrating an uptake amount of a PET probe in a tumor tissue of mice.

An interest region was set on the PET image of the cancer tissue, and a value normalized with a body weight of an individual and an administration radiation dose was used as an accumulation amount of [$^{18}$F]BCPP-EF in the cancer tissue. The results are illustrated in FIG. 4.

Results

It has been found that the growth rate of a cancer cell implanted to a hind leg thigh of a mouse has been decreased according to an irradiation dose of radiation (FIG. 2).

Before the radiation therapy, even when [$^{18}$F]BCPP-EF was administered, accumulation thereof in the tumor tissue was not observed, and the part of the tumor tissue in the PET image was a "negative image". However, two days after irradiation with radiation, accumulation of [$^{18}$F]BCPP-EF in the tumor tissue was increased, and the part of the tumor tissue in which a therapeutic effect was exhibited could be detected as a "positive image". As the irradiation dose of radiation was increased, increase in accumulation of [$^{18}$F] BCPP-EF was observed (FIGS. 3 and 4). Furthermore, the increase in accumulation of [$^{18}$F]BCPP-EF in proportion to the radiation dose continued until seven days after irradiation with radiation (FIGS. 3 and 4).

From the above description, it has been indicated that a diagnostic agent containing a compound (1-0) such as [$^{18}$F]BCPP-EF can diagnose a therapeutic effect at an early stage after starting of a cancer therapy.

The invention claimed is:

1. A method for diagnosing a therapeutic effect on cancer, comprising:
   a step of performing a cancer therapy to a subject contracting cancer,
   a step of administering a compound represented by formula (1-0) to the subject;

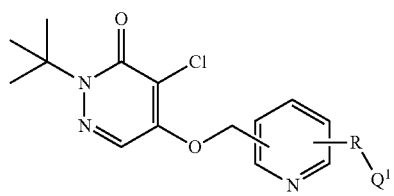

(1-0)

in formula (1-0), R represents —O(CH$_2$)$_n$—, —O(CH$_2$)$_n$OC$_2$H$_4$—, —CH$_2$O(CH$_2$)$_n$—, or —CH$_2$O(CH$_2$)$_n$OC$_2$H$_4$—, n represents an integer of 1 to 5, and Q$^1$ represents F or —OCH$_3$,
a step of detecting the compound in the cancer, and
a step of analyzing an accumulation amount of the compound in the cancer quantitatively.

2. The method according to claim 1, wherein the compound is represented by formula (1-0');

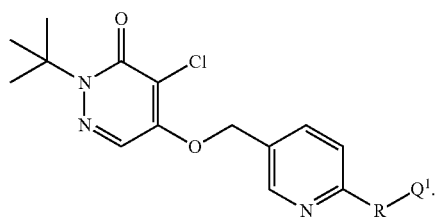

(1-0')

3. A method for diagnosing a therapeutic effect on cancer, comprising:
   a step of performing a cancer therapy to a subject contracting cancer,
   a step of administering a compound represented by formula (1-0) to the subject;

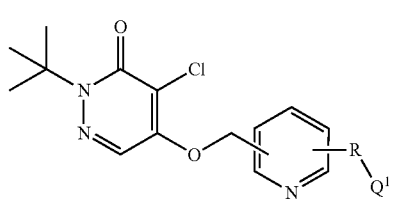

(1-0)

in formula (1-0), R represents —O(CH$_2$)$_n$—, —O(CH$_2$)$_n$OC$_2$H$_4$—, —CH$_2$O(CH$_2$)$_n$—, or —CH$_2$O(CH$_2$)$_n$OC$_2$H$_4$—, n represents an integer of 1 to 5, and Q$^1$ represents $^{18}$F or —O$^{11}$CH$_3$,
a step of detecting the compound in the cancer, and
a step of analyzing an accumulation amount of the compound in the cancer quantitatively.

4. The method according to claim 3, wherein the compound is represented by formula (1-0');

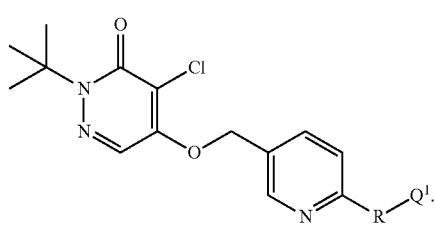

(1-0')

5. The method according to claim 3, wherein the compound is detected by positron emission tomography (PET).

6. The method according to claim 4, wherein the compound is detected by positron emission tomography (PET).

7. The method according to claim 1, wherein the subject is a human.

8. The method according to claim 3, wherein the subject is a human.

9. The method according to claim 1, wherein the cancer therapy is selected from radiation therapy and chemotherapy.

10. The method according to claim 3, wherein the cancer therapy is selected from radiation therapy and chemotherapy.

11. The method according to claim 1, wherein the compound is administered to the subject at two to ten days after the cancer therapy is started.

12. The method according to claim 3, wherein the compound is administered to the subject at two to ten days after the cancer therapy is started.

* * * * *